United States Patent
McGowan, Jr. et al.

(10) Patent No.: US 12,320,147 B2
(45) Date of Patent: Jun. 3, 2025

(54) MANUAL AND AUTOMATIC DISINFECTING DOOR SYSTEM AND METHOD

(71) Applicant: Overhead Door Corporation, Lewisville, TX (US)

(72) Inventors: Paul F. McGowan, Jr., Corpus Christi, TX (US); Federico Romero, Corpus Christi, TX (US)

(73) Assignee: Overhead Door Corporation, Lewisville, TX (US)

( * ) Notice: Subject to any disclaimer, the term of this patent is extended or adjusted under 35 U.S.C. 154(b) by 551 days.

(21) Appl. No.: 17/233,121

(22) Filed: Apr. 16, 2021

(65) Prior Publication Data

US 2021/0324659 A1    Oct. 21, 2021

Related U.S. Application Data

(60) Provisional application No. 63/012,463, filed on Apr. 20, 2020.

(51) Int. Cl.
*E05B 1/00* (2006.01)
*A61L 2/10* (2006.01)
*A61L 2/22* (2006.01)
*A61L 2/24* (2006.01)

(52) U.S. Cl.
CPC .............. *E05B 1/0069* (2013.01); *A61L 2/10* (2013.01); *A61L 2/22* (2013.01); *A61L 2/24* (2013.01); *A61L 2202/14* (2013.01); *A61L 2202/25* (2013.01)

(58) Field of Classification Search
CPC ..... A61L 2/10; A61L 2/22; A61L 2/24; A61L 2202/14; A61L 2202/25; A61L 2/183; E05B 1/0069
See application file for complete search history.

(56) References Cited

U.S. PATENT DOCUMENTS

| | | | |
|---|---|---|---|
| 7,320,418 B2 | 1/2008 | Sassoon | |
| 10,279,061 B2* | 5/2019 | Wyman | A61L 2/0088 |
| 2011/0150698 A1* | 6/2011 | Van Zijl | A61L 2/22 |
| | | | 422/107 |
| 2012/0176241 A1* | 7/2012 | Pasch | A61L 2/10 |
| | | | 250/492.1 |

(Continued)

FOREIGN PATENT DOCUMENTS

WO    2011128652 A2    10/2011

OTHER PUBLICATIONS

European Patent Office, Extended European Search Report, Application No. 21169447.6, Jan. 24, 2022, 7 pages, Munich, Germany.

*Primary Examiner* — Sean E Conley
*Assistant Examiner* — Brendan A Hensel
(74) *Attorney, Agent, or Firm* — Haynes and Boone, LLP (57) ABSTRACT

A self disinfecting door system and method is described, including: a door, and an ultraviolet (UV) light in the proximity of the door and configured to shine at at least a portion of the door when activated. The UV light may be directed at the door to the exclusion of other portions of the surrounding environment. The UV light is mounted on the wall or floor proximate the door. Additionally, there may be a nozzle adjacent the door and configured to release a disinfecting fluid directed at the door when activated.

15 Claims, 7 Drawing Sheets

(56) References Cited

U.S. PATENT DOCUMENTS

| | | | |
|---|---|---|---|
| 2012/0305804 A1* | 12/2012 | Goldman | E05B 1/0069 |
| | | | 250/492.1 |
| 2016/0128886 A1* | 5/2016 | Merino | E04H 1/1277 |
| | | | 600/21 |
| 2017/0049915 A1* | 2/2017 | Brais | H05B 47/115 |
| 2017/0246332 A1* | 8/2017 | Marshall | E05B 1/0069 |
| 2018/0117194 A1* | 5/2018 | Dobrinsky | G01N 21/6486 |
| 2018/0154032 A1* | 6/2018 | Dombrowsky | A47L 11/405 |
| 2018/0339075 A1 | 11/2018 | Kennedy et al. | |

* cited by examiner

MANUAL AND AUTOMATIC DISINFECTING DOOR SYSTEM AND METHOD

PRIORITY CLAIM

This patent application claims the benefit of the filing date of U.S. Provisional Application 63/012,463, filed Apr. 20, 2020, incorporated herein in its entirety by reference.

TECHNICAL FIELD

This patent disclosure relates generally to manual and automatic door systems and, more particularly, to self-disinfecting door systems.

BACKGROUND

Door systems are used to selectively provide access to areas and buildings. Some door systems may provide security by limiting access to unauthorized persons while allowing access to authorized persons. Further, door systems may allow many people to move through the door system in a relatively short amount of time.

Due to the fact that many people may move through door systems, it is likely that the door system may be contaminated with germs such as bacteria, viruses, microorganism or other contaminates. Current door systems are cleaned by hand which is a labor-intensive and often a time-consuming process. Further, often the door system is taken out of service in order to clean it. It would be desirable to have a door system that can be cleaned without the manual labor intensive and time consuming process currently used.

SUMMARY

The foregoing needs are met to a great extent by embodiments in accordance with the present disclosure, wherein, in some embodiments allows a door system to be self-cleaning and/or disinfecting.

In one aspect, the disclosure describes a door; and an ultraviolet (UV) light in the proximity of the door and configured to shine at at least a portion of the door when activated, wherein the UV light is directed at the door to the exclusion of other portions of a surrounding environment.

In another aspect, the disclosure describes a method comprising sensing a condition of a door system with a sensor; and based upon the sensed condition, activating at least one of an ultraviolet (UV) light and an application of a disinfecting fluid on the door system; wherein the UV light is directed at a door of the door system to the exclusion of other portions of a surrounding environment.

In yet another aspect, the disclosure describes a control system comprising a sensor configured to detect a condition of a door of a door system, a controller configured to activate at least one of either an ultraviolet (UV) light disposed in the proximity of the door and directed at the door to the exclusion of other portions of a surrounding environment and an application of a disinfecting fluid directed at a door system.

In yet another aspect, the disclosure describes a door system comprising: an infrared sensor configured to monitor a temperature of a person approaching or moving through a door system, and a controller in communication with the infrared sensor, the controller being configured to activate an indicator if the temperature exceeds a threshold limit.

These aspects of the invention have been described in order that the detailed description thereof herein may be better understood, and in order that the present contribution to the art may be better appreciated. There are additional aspects of the invention that will be described below.

The present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

Figure 1:
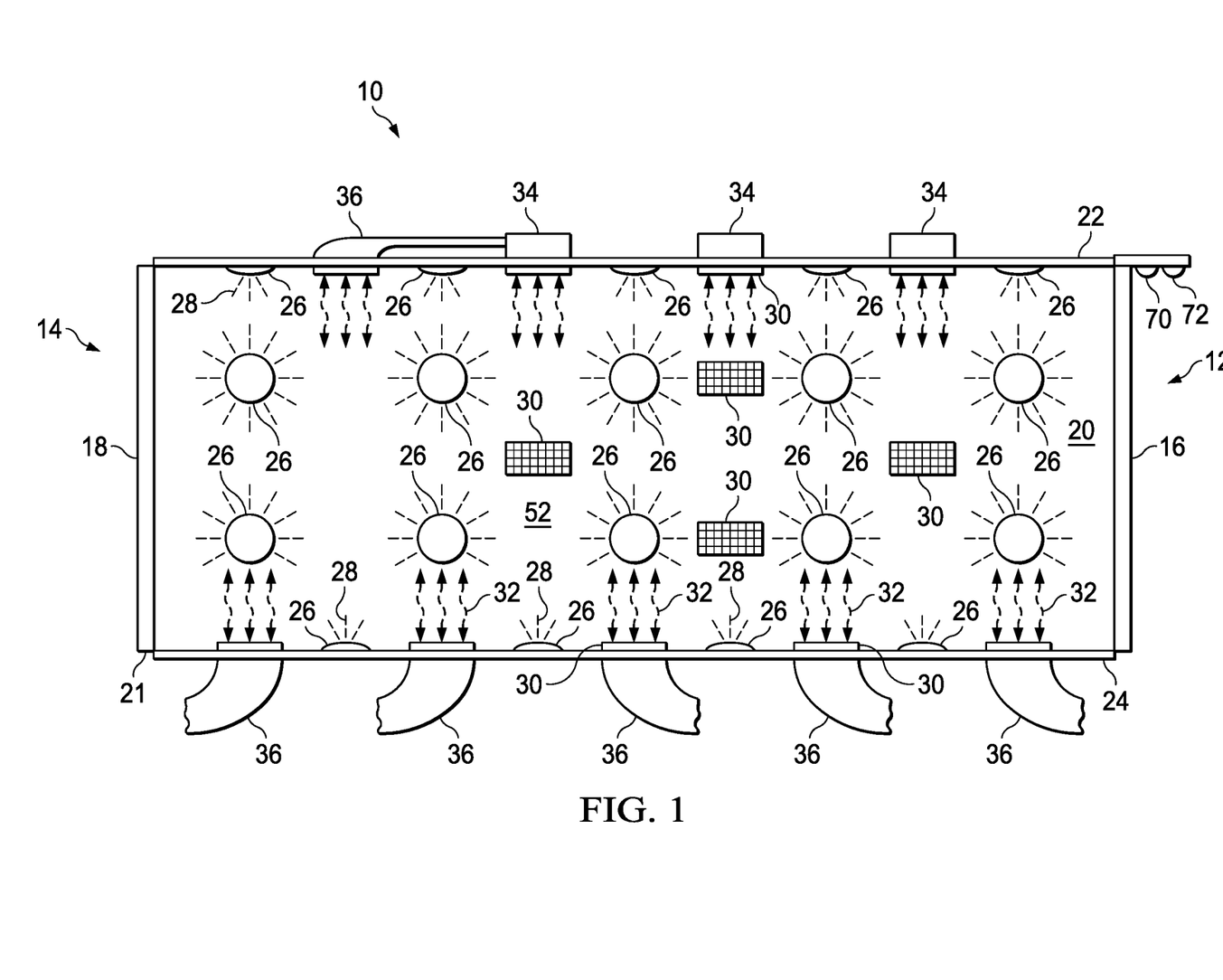
FIG. 1 is a side view of a self-disinfecting secure lane door system in accordance with the present disclosure.
Figure 2:
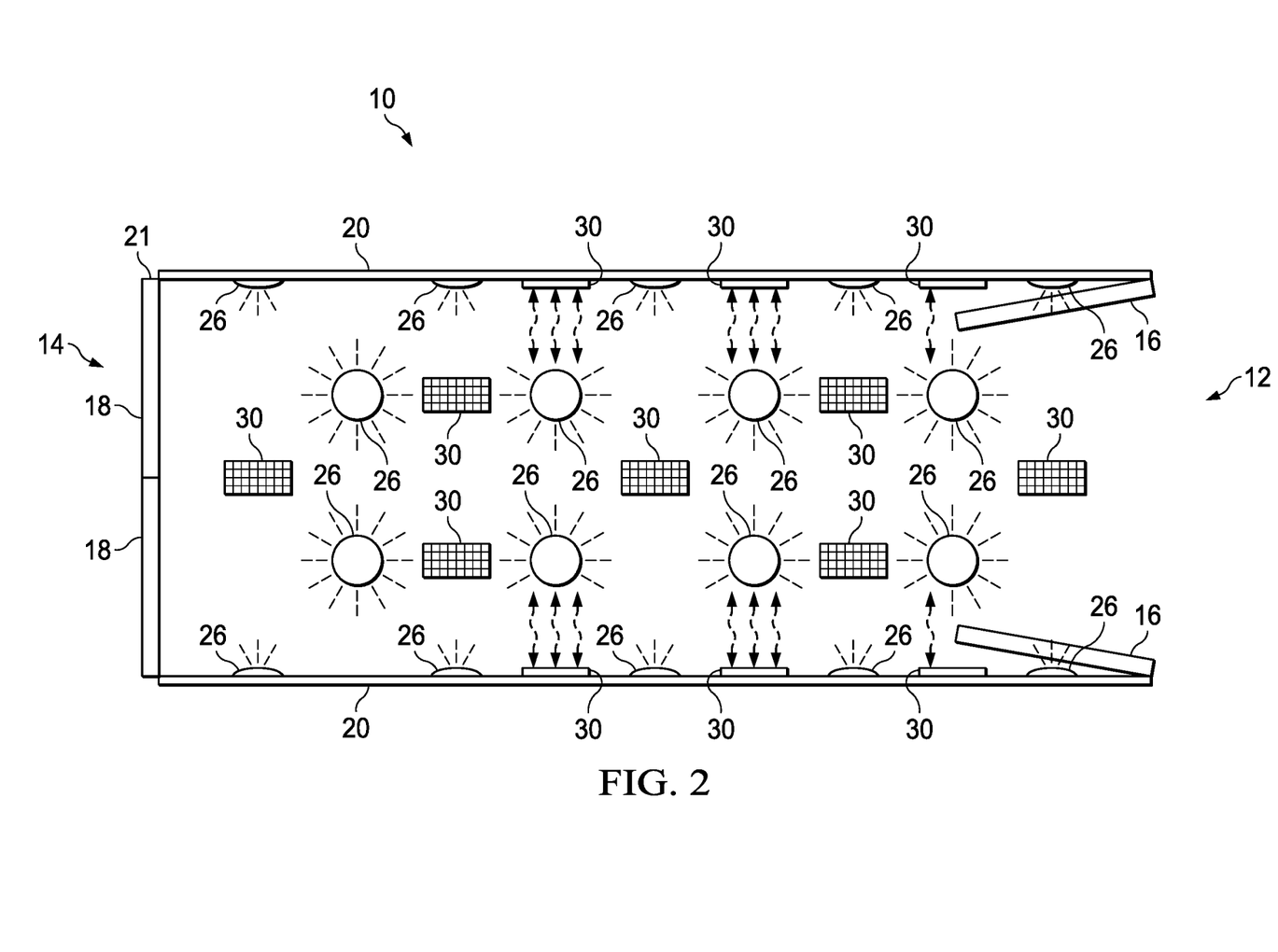
FIG. 2 is a top view of a self-disinfecting secure lane door system in accordance with the present disclosure.

Self-disinfecting door systems 10 shown in the FIGS. and described herein are exemplary and not exhaustive of the types of door systems that may be self-disinfecting in accordance with the present disclosure. FIGS. 1 and 2 are side and top views of a secure exit lane type door system 10 that is also self-disinfecting. The door system 10 of FIGS. 1 and 2 include an entry way 12 and an exit way 14. The entry way 12 is equipped with a pair of entry way doors 16 and the exit way 14 is also equipped with exit way doors 18. It will be understood that in some instances people or other objects may move through the door system 10 in such a way that the entry way 12 is and exit way 14 and vice versa. In such instances, the exit doors 18 become entry doors 16 and vice versa. The words "entry" and "exit" are meant to aid the reader in understanding and are not used as limiting terms. The door system 10 of FIGS. 1 and 2 includes a ceiling 22 and floor 24. The door system 10 of FIGS. 1 and 2 operate, in some respects, generally as known for secure exit lanes and as described, for example, in U.S. patent application Ser. No. 16/267,520 titled "Secure Exit Lane Door" filed Feb. 5, 2019, and incorporated herein by reference in its entirety.

Figure 3:
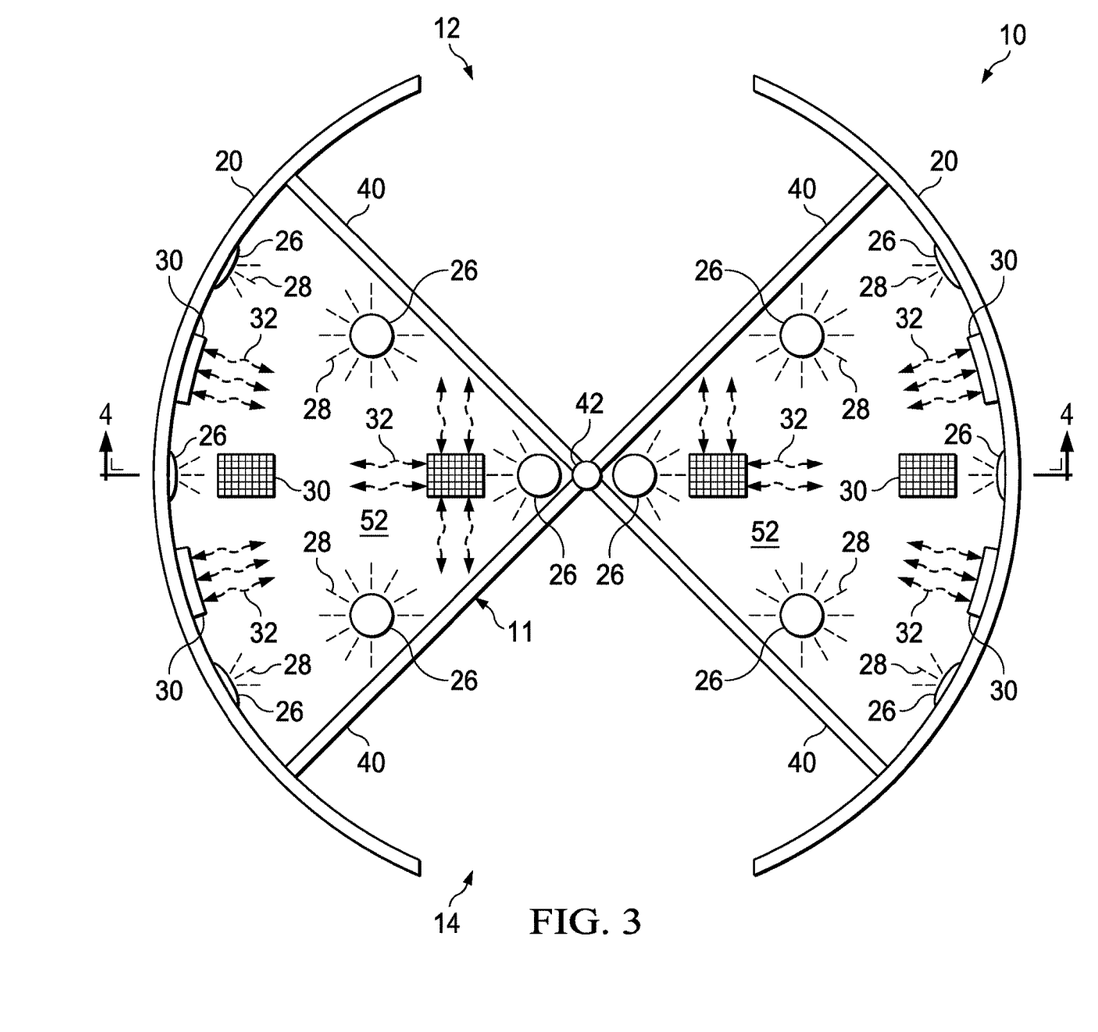
FIG. 3 is a top view of a self-disinfecting revolving door system in accordance with the present disclosure.
Figure 4:
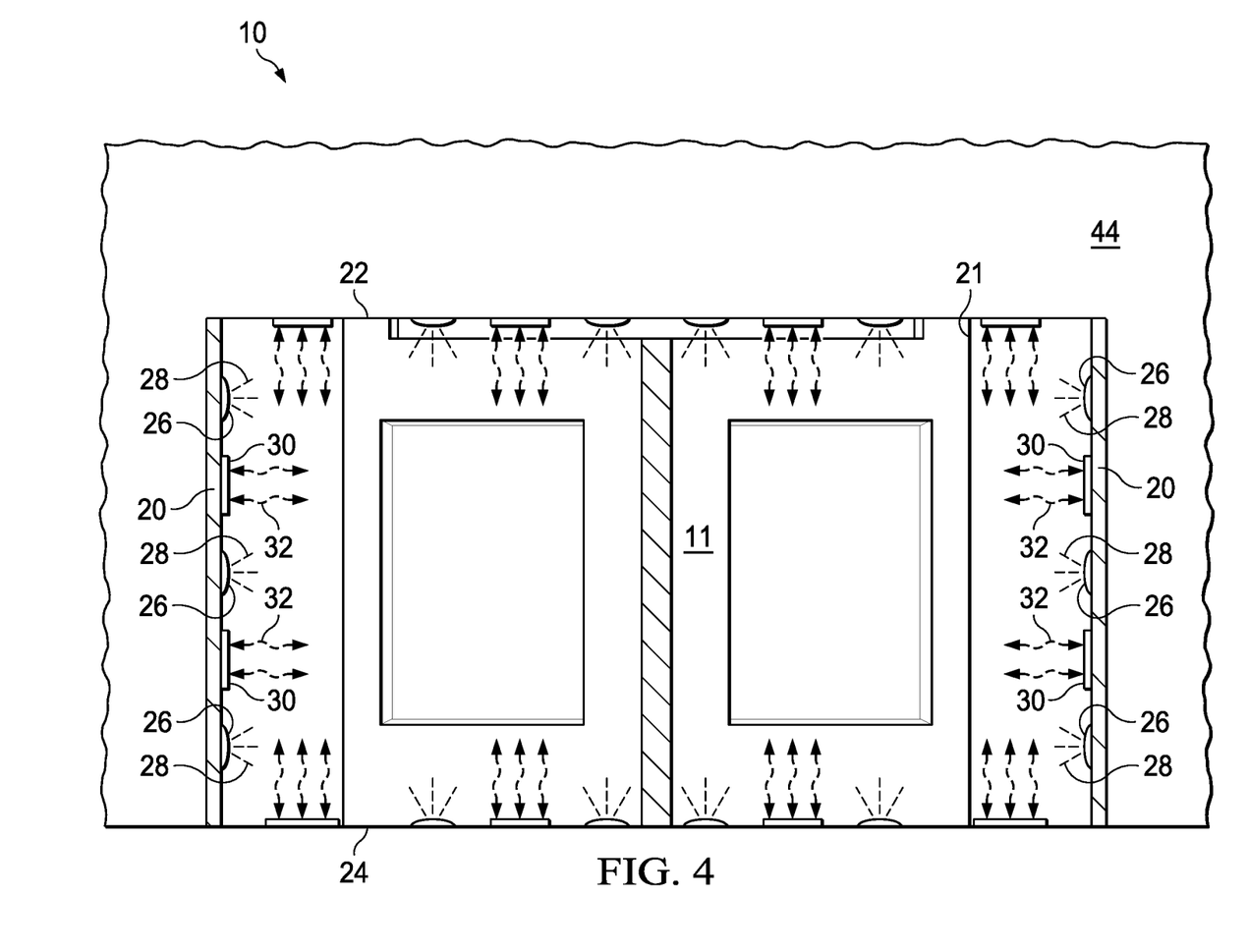
FIG. 4 is cross-sectional view taken of lines 3-3 in FIG. 3 of a self-disinfecting revolving door system in accordance with the present disclosure.

FIGS. 3 and 4 are top and front (and also rear) views of a revolving door system 10 in accordance with the present disclosure. FIG. 4 illustrates a cross section through lines 4 of FIG. 3. The revolving door system 10 has a door 11 which has wings 40 which rotate about a central shaft or axis 42. While door 11 with four wings 40 is shown, other revolving door systems 10 in accordance with the present disclosure may use other amounts of wings 40 such two, three, five or more or fewer. The revolving door system 10 may be, manually operated, powered, or manual with power assist as known for revolving doors. Revolving door systems are known, so for brevity, common details will not be described in detail. Wall 44 may surround the area in which door 11 is installed.

Figure 5:
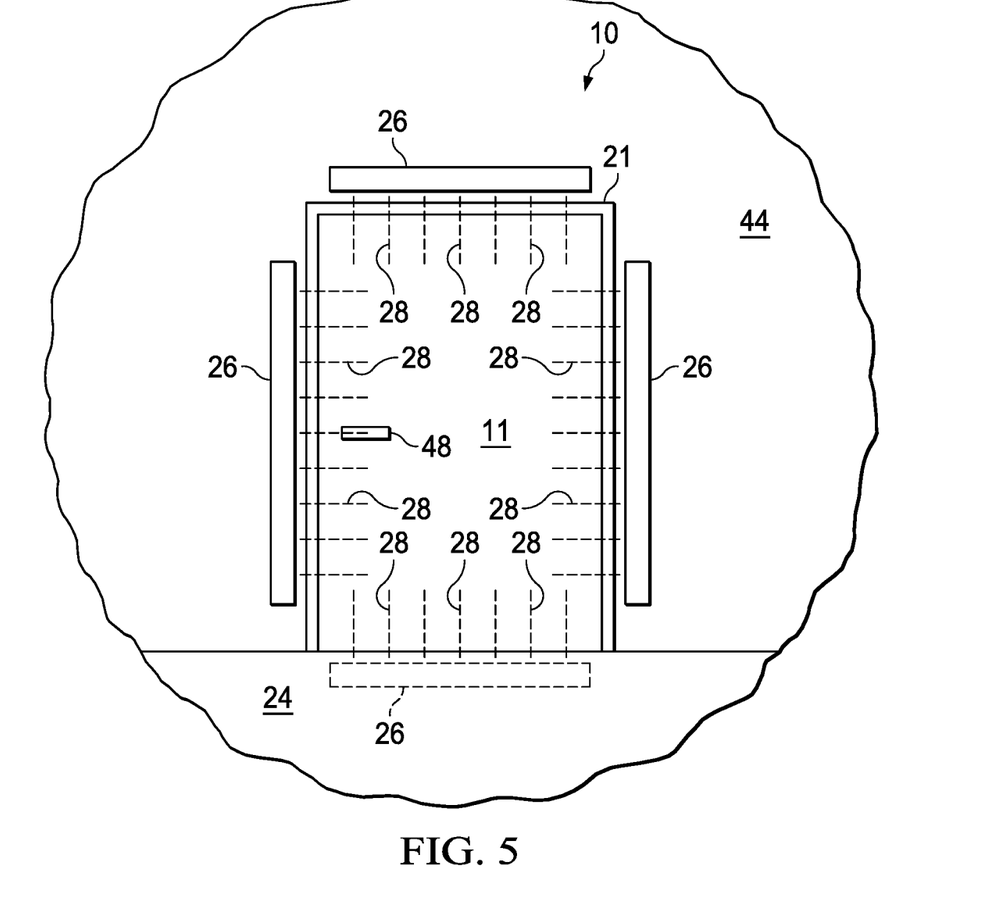
FIG. 5 a front (or rear) view self-disinfecting door system in accordance with the present disclosure.
Figure 6:
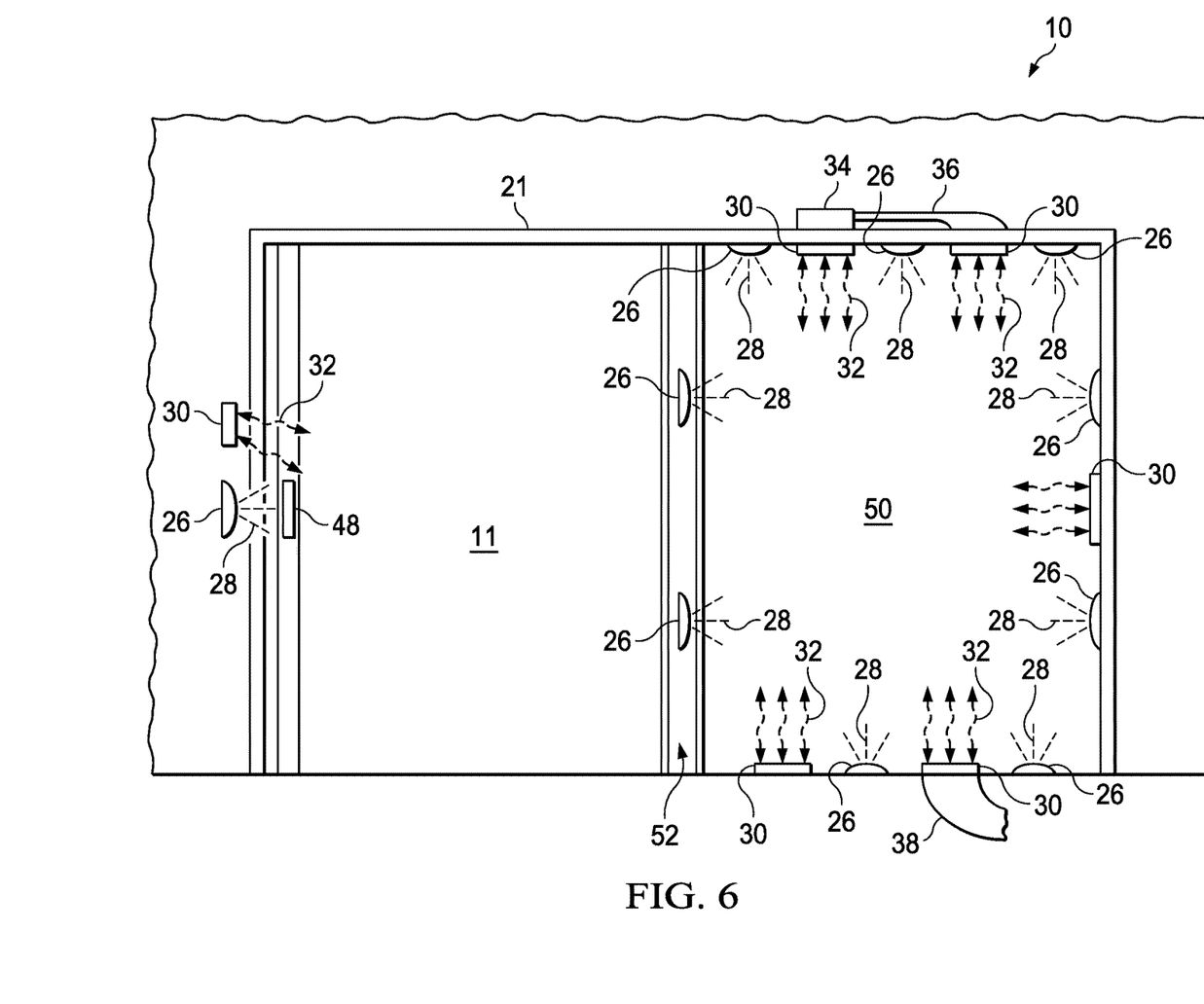
FIG. 6 is a front (or rear) view of a a self-disinfecting sliding door system in accordance with the present disclosure.

FIG. 5 shows a front (or rear) view of a door system 10 which incorporates a typical door 11 mounted on hinges in a door frame 21 surrounded by wall 44. Hinged doors 11 are known, so for brevity, common details will not be discussed in detail. FIG. 6 is a front (or rear) view of a sliding door system 10. The sliding door system 10 generally operates, in some respects, as a typical sliding door 11, so for brevity, common details of a sliding door 11 will not be discussed.

The distinguishing features illustrated in FIGS. 1-6 may be added to existing door systems 10 or may be incorporated into new door systems. These distinguishing features allow the door systems 10 to disinfect themselves so that the door systems 10 can host fewer or no harmful viruses, bacteria or other microorganisms compared to door systems 10 lacking these features. Those distinguishing features will be discussed below.

Ultraviolet (UV) light may kill or otherwise render harmless viruses, bacteria or other microorganisms. Further, Ozone (O3) may also kill or otherwise render harmless viruses, bacteria or other microorganisms. In some embodiments, door systems 10 incorporate the use of UV light and/or Ozone to disinfect the door systems 10.

As shown in FIGS. 1-6 door systems 10 may be equipped with UV lights 26 configured to shine ultraviolet light on the door system 10 to disinfect the door system 10. For purposes of illustration in the FIGS. the UV lights 26 have light rays 28 extending from them, but in some aspects no visible light rays 28 can be seen. Furthermore, the number, shape and placement of the UV lights 26 is meant to be exemplary and not limiting. The UV lights 26 that may be used may be standard off-the shelf UV lights available or any other suitable UV lights 26.

The UV lights 26 may be mounted to any of the ceiling 22, floor 24, the door 11, 16, 18, the door frame 21, or side walls 20 (in door systems 10 that have side walls 20). The UV lights 26 are oriented to shine back on the door system 10 to disinfect it. In the embodiments as shown in FIGS. 1-6, it will be appreciated that the number and orientation of the UV lights 26 may be selected shine on all parts of the door system 10 that are desired to be disinfected.

In some embodiments such as the one shown in FIG. 5, the UV lights 26 may extend from the side walls 20, or over the door 11, and shine back on the door 11. In some aspects, the UV lights 26 when mounted on the wall 20 may be mounted to the side of the door 11, and protruding from the wall 20 such that they may be directed back to shine on the surface of the door 11 and/or door elements such as handle 48. Likewise, UV lights 26 mounted on the wall 20 above the door 11 may protrude from the wall 20 and shine light back on the surface of the door 11 and/or door elements such as handle 48. UV lights 26 mounted on the floor 24 may be mounted in a housing that protrudes above the floor 24 and is placed to the side so that the housing does not impede passage through the door 11. In some aspects, the UV lights 26 may be mounted in a housing which is recessed in the floor 24 so that the surface of the floor 24 is maintained level. A material which is transparent to UV rays may be placed over the recessed UV lights 26 such that a person could temporarily step over the UV lights 26 without damaging them. Additionally, UV lights 26 may shine on the door 11 from the floor 24 or from above the door 11. In the implementation of FIG. 5, the UV lights 26 extend linearly in a direction substantially parallel to an edge (including side, top, or bottom) of the door 11.

In some implementations, the UV lights may be disposed to direct UV light onto the door. As used herein, directing light at or onto the door means that the UV lights are disposed to shine primarily at the door to the exclusion of other space not directly adjacent the door. For example, a hood, fixture base, or reflector may be used to direct UV light at the doors to the exclusion of some areas not directly adjacent the doors. Having UV lights disposed to shine primarily at the door is different than a UV light merely disposed in a room to emit light generally about the room. In some implementations, this includes directing light exclusively at the door and the walls, floor, or ceiling directly adjacent the door. This may distinguish the use of a UV lamp generally disposed within a room without being directed at a door. That is, as contemplated herein, some implementations of the UV lights are directed at the door. In addition, some UV lights are disposed in the proximity of the door. As used herein, "proximity of the door" means that the UV lights are disposed between about 0 and six feet of the door. Having UV lights in the proximity of the door increases the capacity of the UV lights to disinfect the door and may be again distinguish from a UV light merely disposed in a room.

In addition to, or instead of UV lights 26, some embodiments may also use disinfecting fluids such as ozone ($O_3$). Fluid vents 30 may be located on the door system 10 to direct disinfecting fluids on the door system 10. The fluid may be a gas such as ozone, or in other embodiments, the fluid may be a disinfecting liquid. When disinfecting liquids are used, the vents 30 may be or include nozzles used to direct the liquid on portions of the the door system 10 desired to be disinfected. The liquid may be any suitable disinfecting liquid.

In embodiments where the fluid is a liquid, vents 30 at lower portions of the door system 10 may be used to drain excess disinfecting liquid. Drainage ducts 38 may carry the liquid to an appropriate disposal system.

The vents 30 may receive disinfecting liquid via ducts 36. For example, when the fluid is ozone, the vents 30 may receive ozone via ducts 36 from an ozone source 34 which may be an ozone generator which generates ozone from the air, $O_3$ tanks or other ozone source.

In some embodiments, both UV lights 26 and disinfecting fluid (either liquid or gas) are utilized. They may be used simultaneously, the UV lights 26 shining on the door system while disinfecting liquid is being released from the vents 30. The UV lights 26 may also be used at different times than the disinfecting fluid. The UV lights 26 may be used more often, for instance every time the door 11 opens and closes they go through a cleaning mode using the UV lights 26. Then after some time has elapsed, for example during the night, or after the door 11 has not been used for a predetermined amount of time, the disinfecting fluid may be applied. In this way the disinfecting fluid is conserved and is less likely to spray when someone is present. In some embodiments, the UV lights 26 and the disinfecting fluid alternate when they are used.

In some embodiments, the door system 10 defines a space 52 (see FIGS. 1, 3, 6) where the space 52 is enclosed by the door system 10. For example, in FIG. 1 when the entry doors 16 and exit doors 18 are all closed, the space 52 within the exit lane is enclosed. In FIG. 3, when the revolving door 11 is in certain positions, a space 52 is created between the side walls 20 and the door 11. In the sliding door system 10 of FIG. 6, a space 52 is created between the door 11 and the stationary part 50. The size of the space 52 in a sliding door system 10 may vary depending upon the position of the sliding door 11. In some embodiments, the air in this space as well as the surfaces of the door assembly 10 that define this space may be disinfected by fluid flowing through the vents 30. The fluid may also be removed from the space 52 by venting the fluid out of the space 52 either back through the vents 30 or dedicated space venting ducts 36. The two jagged two arrow headed lines 32 are used to illustrate the fluid to exit the vents 30 and, in some instances to be vented back through the ducts 36. In some implementations, such as the secure entry systems in FIGS. 1-4, the UV lights 26 and/or the vents 30 are intermittently spaced in the area between the exit doors and entry doors. In this way, disinfection may be accomplished using overlapping beams of UV rays from a plurality of different sources. For example, the UV light may be emitted from UV lights 26 on a) a wall and ceiling or b) a wall and floor or c) ceiling and floor, or d) wall and an opposing wall. In some implementations, the UV lights shine from multiple directions or angles onto the door itself, as in FIGS. 5 and 6. In some implementations, as noted herein, the lights may be focused or directed at the door.

To further the capability of the door systems 10 to disinfect, door handles (door knobs) 48 (shown best in FIGS. 5 and 6) and other common parts that are often touched by users going through the door system 10 such as grab bars, push plates, and other commonly touched features of a door system 10 may be made or coated with a self-disinfecting substance. For example, silver and copper as well as alloys of each, along with certain nanoparticles, are known to be toxic to or otherwise render harmless certain viruses, bacteria or other microorganisms. As such, door handles 48 and other parts of door systems 10 commonly touched by users of a door system 10 may be made or coated with silver, copper, or other self-disinfecting substance.

In addition to, or in the alternative, UV lights 26 may be positioned to shine on the handles 48 as shown in FIG. 6. In some embodiments, as also shown in FIG. 6, vents or nozzles 30 may be positioned to direct disinfecting fluid onto the handle 48 or other hardware desired to be disinfected.

Figure 7:
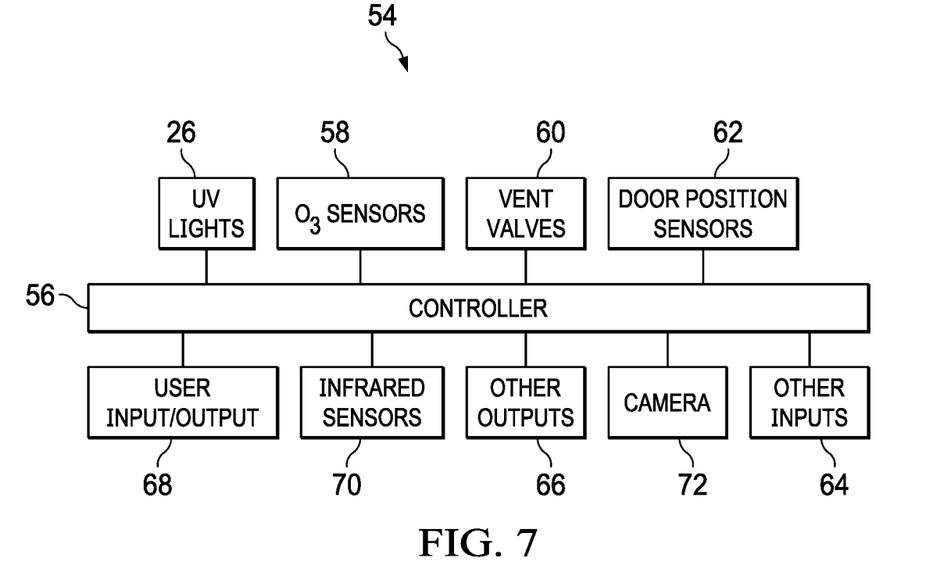
FIG. 7 is a schematic diagram of a control system for a self-disinfecting door system in accordance with the present disclosure.

FIG. 7 illustrates a schematic diagram of a door system 10 control system 54 for controlling the disinfecting features of the door system 10. The control system 54 includes a controller 56 which may be a microprocessor or other suitable controller. The controller 56 may be operatively connected to the UV lights 26 to turn them on or off. In some embodiments, the controller 56 may be in communication with an actuator responsive to signals from the controller 56. The actuator may be configured to to move the UV lights 26 (such as, but not limited to, pivoting the UV lights) or otherwise direct where the UV lights 26 shine. The controller 56 may move the UV lights 26 automatically and/or based on a user configuration. In some aspects, the light is able to focus and defocus to target more directly portions of the door 11. The UV lights 26 may be controlled to sequentially shine light over different portions of the door 11. The portions of the door 11 may be illuminated roughly the same amount of time, or predetermined portions of the door 11 may be illuminated for longer or at a higher intensity. For example, portions of the door which are touched by people more often may be preferentially illuminated. Optionally $O_3$ sensors (or other fluid disinfectant detecting sensors) 58 are operatively connected to the controller 56 to inform the controller 56 of the presence of a disinfectant.

In some embodiments, the vent valves 60 are operatively connected to the controller 56. The controller 56 and vent valves 60 are configured to 30 to control disinfecting fluid moving through the vent ducts 36, 38 and vents 30. For example, disinfecting fluid may need to be directed toward the vents 30 during a disinfecting operation or away from the vents 30 through the draining ducts 38 when excess disinfecting fluid is being drained from the door system 10.

Optionally, door position sensors 62, are positioned in the door system 10 to detect a position of the door 11. The door position sensors 62 are operatively connected to the controller 56 to send signals to the controller 56 representative of the door 11 position.

In some embodiments, the controller 56 can clean the door 11 in several ways. For example, the controller 56 may do a cleaning operation on the door 11 when the door 11 is in a specific position, at timed intervals, or sense with other inputs 64 that there are no users moving through the door system 10. In some embodiments, the door system 10 may go into a cleaning mode. This may be a maintenance mode to clean the door 11 when users are not present. The door system may lock the door 11 while in door 11 cleaning mode until either the cleaning process is finished after a predetermined time, or a sensor detects someone approaching and/or the door opening. Other combinations of inputs to the controller may be used to determine when to start and stop a cleaning mode. For example, the cleaning mode may be configured to run on a timed interval, but before starting the cleaning operation the controller may check a sensor to ensure that nobody is close to the door. Presence of a person may be determined based on a infrared sensor 70, motion sensor, or other sensor.

In addition to outputs such as controlling the UV lights 26 and valving the disinfecting fluid, the controller 56 may have other outputs 66 such as communicating to a remote monitor or a janitorial or maintenance service to indicate the door system 10 is in need of service. In some embodiments, the controller 56 may communicate via other inputs 64 and/or outputs 66 with a controller of the door 11. In other embodiments, the controller 56 maybe part of or integrated with the door 11 controller (which controller controls operation of powered or power assist door systems 10.

In some embodiments, a user input/output 68 which could be a keypad, a plug-in device, a wireless device such as a phone or notebook computer, a laptop computer or similar device operatively connected to the controller 56. The input/output 68 can input commands to the controller 56 and/or receive signals which can provide information (requested or pushed) regarding the controller 56, the UV lights 26, sensors 58, fluid sources 34, valves 60, door 11 position, or information from other inputs 64 or out puts 66. The user input/output 68 will allow a user or operator of the door system 10 to operate and/or monitor the cleaning features of the door system 10.

In some embodiments, the door system 10 may include infrared sensors 70 (see FIGS. 1 and 7). The infrared sensor 70 or sensors 70 can be oriented in the door system 10 to monitor and/or measure the temperature of a person (or object) moving or attempting to move through the door system 10. The infrared sensor(s) 70 may be oriented to measure the temperature of a person approaching the door system 10. As shown in FIG. 7, the infrared sensor(s) 70 may be operatively connected to the controller 56. The controller 56 may be configured to do any number of things if the infrared sensor(s) 70 indicate that a person's temperature is above a threshold temperature that may be stored in the controller.

For example, the controller 56 may activate an indicator, such as an alarm using a speaker or other sound device, an indicator or signaling light, or other indicia, such as a display, that a person's temperature exceeds the threshold. The controller 56 may send a signal through other outputs 65 to a remote monitoring device that indicates a person's temperature exceeds the threshold. Camera(s) 72 (see FIGS. 1 and 7) may capture video and/or still images of the person with the temperature exceeding the threshold. In some embodiments, the controller 56 may cause the door system 10 to lock and not admit access to the person having the temperature exceed the threshold. The controller 56 may lock the door system 10 directly or communicate with a controller that controls the door system 10 to lock the door system 10.

Optionally, the infrared sensor(s) 70 can monitor objects and/or people so that the temperature of objects and/or people can be communicated to the controller 56. The temperature data can be sent to remote monitoring systems or saved locally. People and/or objects with temperatures in certain ranges may cause the controller 56 to carry out any of the actions described above. Threshold temperatures or temperature ranges that warrant monitoring or action can be programmed into the controller 56 (such as, for example but not limited, via the user input/out 68 or remote devices via the other inputs 64) or be factory set.

It will be understood that some door systems 10 may include the disinfecting and/or infrared monitoring features described herein as part of the initial construction of the door system 10. Other door systems 10 may have retro fit disinfecting and/or monitoring features added to the door system 10 after initial construction and/or installation.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

We claim:

1. A door system comprising:
a door;
an ultraviolet (UV) light in the proximity of the door and arranged to shine at at least a portion of the door when activated, wherein the UV light is directed at the door to the exclusion of other portions of a surrounding environment;
a nozzle adjacent the door and configured to release a disinfecting fluid directed at the door when activated;
a position sensor configured to detect a position of the door; and
a controller configured to:
activate the UV light in response to a first signal from the position sensor indicating the position of the door;
detect, based on the first signal and a second signal from the position sensor, that an amount of time since the door has been used has surpassed a predetermined amount of time; and
activate the nozzle in response to detecting that the amount of time since the door has been used has surpassed the predetermined amount of time.

2. The door system of claim 1, wherein the door is in a wall, and the UV light is mounted on the wall adjacent the door such that the UV light protrudes from the wall.

3. The door system of claim 1, wherein the UV light is mounted in a housing disposed proximate to the door.

4. The door system of claim 3, wherein the UV light is contained within a housing recessed in a floor proximate to the door.

5. The door system of claim 1, wherein the controller is configured to selectively simultaneously activate the UV light and the disinfecting fluid.

6. The door system of claim 1, wherein the controller is configured to activate the UV light and the disinfecting fluid at different times based on a mode of operation.

7. The door system of claim 1, further comprising a secure lane, and wherein the door comprises at least one of an entry door or an exit door to the secure lane, the UV light being disposed in the secure lane and disposed to shine on at least one of the entry door or the exit door inside the secure lane.

8. The door system of claim 1, wherein the position of the door is a closed position.

9. The door system of claim 1, wherein the position of the door is an open position.

10. The door system of claim 1, wherein activating the UV light includes moving the UV light, via an actuator, to be directed to a plurality of portions of the door.

11. The door system of claim 10, wherein the UV light is directed to a first portion of the door for a longer period of time than to a second portion of the door.

12. The door system of claim 10, wherein the UV light is directed to a first portion of the door at a higher intensity than to a second portion of the door.

13. The door system of claim 1, further comprising space venting ducts configured to remove the disinfecting fluid from the door system after the nozzle has directed the disinfecting fluid at the door.

14. The door system of claim 1, further comprising a disinfectant sensor configured to detect the presence of disinfecting fluid.

15. A door system comprising:
a door;
an ultraviolet (UV) light configured to shine at at least a portion of the door when activated;
a nozzle configured to release a disinfecting fluid directed at the door when activated;
a position sensor configured to detect a position of the door; and
a controller configured to:
activate the UV light in response to a first signal from the position sensor indicating the position of the door;
detect, based on the first signal and a second signal from the position sensor, that an amount of time since the door has been used has surpassed a predetermined amount of time; and
activate the nozzle in response to detecting that the amount of time since the door has been used has surpassed the predetermined amount of time.

* * * * *